United States Patent [19]

Dorman et al.

[11] 4,066,684
[45] Jan. 3, 1978

[54] PREPARATION OF PEPTIDES

[75] Inventors: Linneaus C. Dorman; Edwin C. Steiner, both of Midland, Mich.

[73] Assignee: The Dow Chemical Company, Midland, Mich.

[21] Appl. No.: 460,840

[22] Filed: Apr. 15, 1974

[51] Int. Cl.$^2$ ............................................ C07C 125/04
[52] U.S. Cl. ............................ 260/112.5 R; 260/349; 560/158
[58] Field of Search ............................. 260/349, 112.5

[56] References Cited

U.S. PATENT DOCUMENTS 3,562,295  2/1971  Pedersen ............................. 260/338

OTHER PUBLICATIONS

K. Kopple, "Peptides and Amino Acids," Benjamin, Inc., New York (1966), pp. 47–48.
M. Bodanszky and M. Ondetti, "Peptide Synthesis," Interscience, New York (1966), pp. 75–81.
E. Schroder and K. Lubke, "The Peptides," vol. 1, Academic Press, New York (1965), pp. 82–85.

*Primary Examiner*—Delbert R. Phillips
*Attorney, Agent, or Firm*—Glwynn R. Baker

[57] ABSTRACT

The preparation of the azide of a carboxylic acid by reacting the hydrazide of the acid with nitrous acid is facilitated by using the organic solvent-soluble complex of an alkali metal nitrite with an ethylene oxide or propylene oxide cyclic polymer as the nitrous acid source. The improvement is particularly useful as a means for making peptides by the coupling reaction of an amino acid ester or other derivative with an acid azide in an anhydrous reaction medium.

1 Claim, No Drawings

PREPARATION OF PEPTIDES

BACKGROUND OF THE INVENTION

This invention is an improvement in a known chemical process. More specifically, it concerns an improved process for making polypeptides by the coupling reaction of an amino acid azide with an amino acid compound in a substantially anhydrous reaction system.

The azides of carboxylic acids are useful chemical intermediates in processes for converting the acids into other types of compounds. For example, the Curtius rearrangement transforms an azide into the corresponding isocyanate for use in making urethanes, ureas, amides or amines. One synthesis of $\alpha$-amino acids proceeds through the azide of an $\alpha$-cyano acid as an intermediate. Azides are of particular interest in the Bergmann synthesis of polypeptides by the coupling reaction of an N-protected amino acid azide with a C-protected amino acid such as the ester, amide, N-substituted amide, or a solvent-soluble salt.

The latter synthesis, in particular, is of interest because of the increasingly intensive work in the field of synthetic polypeptides. These compounds offer a means for understanding the structure and mode of participation of more complex natural polypeptides and proteins in life processes and "tailor-made" polypeptides differing from naturally occurring molecules in predetermined ways provide useful new tools in biochemical and medical research. Complex, naturally occurring polypeptides such as secretin, insulin, and calcitonin have recently been synthesized in the laboratory using a progression of coupling reactions.

The Bergmann synthesis couples amino acid molecules by reacting the amino group of a carboxyl-protected amino acid compound such as the ester, amide, or salt with the acyl azide of an amino acid or peptide wherein the amino group or groups of the azide reactant are protected against undesirable side reactions by an easily removable N-protective group such as an acyl group, a toluenesulfonyl group or a urethane radical.

Generally in azide-amino acid couplings, the azide is made from the corresponding hydrazide by treatment with nitrous acid in aqueous media (e.g., sodium nitrite plus dilute hydrochloric acid) or with an alkyl nitrite in an acidic organic medium. In both cases the azide solution must be washed with base (e.g., bicarbonate solution) to remove excess acid. This step may tend to cause racemization at the $\alpha$-carbon atom of the amino acid or peptide azide. After washing with base, the azide solution is dried prior to reaction with the amino acid compound. Hence, during these manipulations which are time consuming and which must be conducted in the cold, there is greater possibility of rearrangement of the azide to the corresponding isocyanate, a side reaction which may lead to the formation of an urea instead of peptide by the following sequence of reactions:

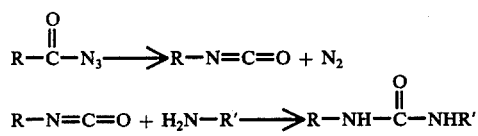

There are special examples in the literature of azide preparations in which, (a) a nonpolar solvent is used in conjunction with an alkyl nitrite as the nitrous acid source with the same reaction vessel and used for both the nitrosylation and coupling reactions excess acid is neutralized with an organic tertiary base; or (b) a polar solvent such as dimethylformamide is used with an inorganic nitrite and hydrochloric acid, to supply nitrous acid, a single reaction vessel is used, and excess acid is neutralized by an organic tertiary base. The present invention, however, has the advantage over the former of using an inexpensive nitrosylating source and over the latter of allowing the use of a nonpolar solvent.

So-called crown complexes of inorganic compounds with macrocyclic polyethers are described by Pedersen in U.S. Pat. No. 3,562,295. These complexes are generally suggested for use in extraction processes and diazotization and nitrosylation reactions although no examples of the latter are given and there is no mention of their possible use in anhydrous polypeptide preparations.

SUMMARY OF THE INVENTION

It has now been found that in the azide coupling reaction for making polypeptides as described above, side reactions and other disadvantages of known procedures are avoided by providing the acid azide reactant as the reaction mixture formed by nitrosylating an N-protected amino acid hydrazide in an essentially anhydrous organic solvent medium using as the source of nitrous acid an alkali metal nitrite complex with a cyclic polymer of ethylene oxide, propylene oxide of mixture thereof.

By this invention, an azide preparation and subsequent coupling of the azide can be carried out in an essentially anhydrous nonpolar solvent or other solvent which permits hydrogen bonding using an inexpensive nitrosylating agent. The entire process is conducted in a single vessel and washing of the azide solution is unnecessary since only a relatively small excess of mineral acid is required and this can be neutralized with an equivalent amount of a tertiary organic base like triethylamine or with an equivalent amount of excess amino reactant.

DETAILED DESCRIPTION

The cyclic polymer of alkylene oxide preferably consists of 4–6 ethylene oxide units and the pentamer is most preferred, because its nitrite complexes are more soluble than those of the tetramer or the hexamer. The preferred alkali metal nitrite is sodium nitrite because of its easy availability and the greater solubility of its cyclic ether complex. Other alkali nitrites such as the potassium and lithium salts are also operable in the process, however. The preferred quantity of cyclic ether is about 2.5–3 mole equivalents based on the nitrite. Lesser amounts may not completely solubilize the nitrite and so may cause slow or incomplete nitrosylation of the acid hydrazide. Larger quantities are merely wasteful. The corresponding cyclic polymers of propylene oxide and cyclic polymers containing both ethylene oxide and propylene oxide units can also be used in the same way to form the nitrite complex.

The nitrosylation process of this invention is carried out by combining the nitrite, alkylene oxide cyclic polymer, and the hydrazide in a suitable solvent which permits hydrogen bonding such as methylene chloride, chloroform, acetonitrile, dimethylformamide, and other such solvents containing at least one carbon-hydrogen bond. To the cooled solution there is then added an excess of a strong acid, preferably a strong mineral acid dissolved in an inert organic solvent. Preferred acids are those whose anhydrous solutions are readily prepared at concentrations of about 2-3 normal. Strong mineral acids or their recognized equivalents such as HCl, $H_2SO_4$, and trifluoroacetic acid are representative of the class. The amino acid ester or other C-protected amino acid compound is then added, preferably dissolved in the same solvent.

The temperature conditions and relative proportions of reactants are those customarily employed in similar known azide preparations and coupling reactions. Since an equivalent of nitrous acid is required to nitrosylate one equivalent of carboxylic hydrazide, at least one equivalent of alkali metal nitrite is necessary for completion of this reaction. A substantial excess, i.e., >5% of nitrite, would lead to an excess of nitrous acid which if not destroyed would attack an amino acid reactant when it is added to the reaction mixture thereby diminishing it and producing complex by-products. An equivalent of acid is necessary to generate an equivalent of nitrous acid. An excess of acid outside the preferred range may tend to destroy acid-sensitive protective group(s) of the carboxylic hydrazide which is undesirable. The preferred amount of amino acid reactant for a subsequent coupling reaction is the amount necessary to neutralize excess acid plus an equivalent amount required for the coupling reaction. If the amount of amino acid reactant is less than the preferred amount, there will be an insufficient amount of it available for the coupling reaction since irreversible neutralization with excess acid will occur first. If the amount of amino reactant substantially exceeds the preferred limit, i.e., >50%, the resulting basic condition of the medium may tend to cause racemization of the carboxylic azide. If the amino reactant is precious then it is preferred that excess acid be neutralized with an equivalent of tertiary amine. The preferred temperature range for the nitrosylating step is $-15°$ to $-25°$. Working above this temperature may tend to cause rearrangement of the axide to an isocyanate. Further, a protective group such as the tertiary butyloxycarbonyl radical may be susceptible to acid attack when operating above the preferred range. Nitrosylating below the preferred range may lower the solubility of the reactants which is undesirable. The preferred temperature for the amino ester coupling step is $-15°$ to $-20°$ for the first 1-2 hours, then $0°-5°$ for the remainder of the reaction. Coupling above the preferred temperature may cause undesirable side reactions and coupling below the preferred temperature may lower the solubility of the reactants and slow the reaction rate.

EXAMPLE

Methyl ε-aminocaproate hydrochloride and N-carbobenzyloxy-ε-aminocaproic acid were prepared by procedures described by Garmaise et al., J. Am. Chem. Soc., 80, 3332 (1958) and Zahn et al., Chem. Ber., 90, 320 (1957) respectively.

Methyl N,N'-Dicarbobenzyloxy-ε-aminocaproyl-L-lysinate

To a stirred suspension of 7.0 g. (0.021 mole) of methyl Nε-carbobenzyloxy-L-lysinate hydrochloride and 5.6 g. (0.021 mole) of N-carbobenzyloxy-ε-aminocaproic acid in 50 ml. of methylene chloride was added 2.95 ml. (0.021 mole) of triethylamine. The resulting solution was cooled to 0° C. whereupon 4.6 g. (0.022 mole) of dicyclohexylcarbodiimide was added. Stirring was continued at 0° for 3 hours and the reaction mixture was filtered, the filter residue (dicyclohexylurea) was rinsed with 30 ml. of $CH_2Cl_2$. The combined filtrate and rinse was washed successively with 1N HCl, water, bicarbonate solution and water, dried ($MgSO_4$) and freed of solvent in vacuo. The residue, a thick oil 11.7 g., crystallized on standing and was recrystallized from dilute ethanol. There was obtained 8.1 g. (71%) of pale cream white solid, m.p. 89°-91°. The analytical sample was obtained by another recrystallization from dilute alcohol and dried in vacuo over solid KOH, m.p. 92°-94.5°, $[\alpha]_D^{25} = -11.9° \pm 0.6°$ (0.62 g. in 100 ml. ethanol solution). Infrared and elemental analyses were consistent with the assigned structure.

N,N'-Dicarbobenzyloxy-ε-aminocaproyl-L-lysine Hydrazide

To a warm solution of 7.30 g. (0.0135 mole) of methyl N,N'-dicarbobenzyloxy-ε-aminocaproyl-L-lysinate in 50 ml. of warm absolute ethanol was added 20 g. (0.06 mole) of 95% hydrazine. The resulting solution on cooling and standing at room temperature produced a white precipitate which was collected after about ca. 15 hours, washed with alcohol and dried, 6.9 g. (59%), m.p. 167°-168° and 169°-170° after recrystallization from absolute ethanol, $[\alpha]_D^{25} - 3.7°$ (1.08 g. in 100 ml. DMF solution). Elemental analysis confirmed the identity of the product.

Methyl N,N'-Dicarbobenzyloxy-ε-aminocaproyl-L-lysyl-ε-aminocaproate

To a stirred solution of 72 mg. (1.04 mmole) of sodium nitrite and 610 mg. (2.77 mmoles) of ethylene oxide cyclic pentamer in 7 ml. of methylene chloride was added 542 mg. (1.0 mmole) of N,N'-dicarbobenzyloxy-ε-aminocaproyl-L-lysine hydrazide. This stirred suspension was cooled to $-22°$ C. whereupon 597 mg. (1.88 m equiv.) of HCl in dimethoxyethane (3.1 m equiv. HCl/g. solution) was added dropwise during 5 min., the reaction temperature being maintained between $-22°$ to $-17°$ C. as complete solution resulted. After stirring with continued cooling at $-20°$ to $-17°$ C. for 20 min. the solution was negative to starchiodide paper indicating complete consumption of nitrous acid. Several minutes later a solution of 300 mg. (2.07 mmoles) methyl ε-aminocaproate in 3 ml. of methylene chloride was added during 5 min. at $-20°$ to $-17°$ C. After stirring at ca. $-20°$ C. for 1 hour, the reaction mixture was refrigerated for two days. It was filtered under suction and the filtrate evaporated leaving a semi-solid residue which was triturated with water, collected on a filter and dried yielding 658 mg. of crude white product. This was dissolved in 13 ml. of methylene chloride and filtered to remove some insoluble material; evaporation of the filtrate left 649 mg., of which 624 mg. was recrystallized from 10 ml. of ethyl acetate and 15 ml. of ether, 555 mg. of white solid was recovered. A 551 mg. portion of this was then chromatographed on a column of silica gel which was developed with 100 ml. of methylene chloride followed by 500 ml. of methylene chloride containing 2.5% (by volume) methanol. Fractions containing pure product, as indicated by thin-layer chromatography, were combined and evaporated leaving 478 mg. of white crystalline solid of methyl N,N'-dicarbobenzyloxy-ε-aminocaproyl-L-lysyl-ε-aminocaproate, m.p. 101°-102° C. The yield was 76% (after adjustment for the small amounts removed during the purification steps). The product was identified by infrared spectrum and mixed melting point with a known sample prepared by a conventional coupling procedure. This compound, when converted to the phosphoric acid salt of the amino ester, has fungicidal activity and kills organisms such as Trichoderma sp. when applied as a water solution of 500 ppm. or greater concentration. In a coupling reaction similar to that shown above, N-p-tolylsulfonylglycine hydrazide is reacted with an alkali metal nitrite-ethylene oxide cyclic polymer and HCl by the procedure of this invention to make N-p-tolysulfonylglycine azide and the methyl ester of alanine is added to the cooled reaction mixture to produce N'-(N-p-tolylsulfonylglycyl)alanine. This and other similar reactions are also carried out in the same way using the complex of an alkali metal nitrite with a propylene oxide cyclic polymer or the cyclic polymer of mixed ethylene and propylene oxides. Other such N-protected amino acid azides are readily prepared by this procedure and directly reacted in anhydrous systems with amino acid esters as described herein to make polypeptides in good yield and without significant side reactions. Polypeptides such as the ethyl ester of N-p-toluenesulfonyl-S-benzyl-L-cysteinyl-L-tyrosyl-L-leucine and the methyl ester of N-carbobenzyloxy-L-leucyl glycine are thereby obtained.

We claim:

1. In the process for making methyl N,N'-dicarbobenzyloxy-ε-aminocaproyl-L-lysyl-ε-aminocaproate by reacting the azide of N,N'-dicarbobenzyloxy-ε-aminocaproyl-L-lysine hydrazide with methyl ε-aminocaproate, the improvement wherein said azide is provided as the reaction mixture formed by nitrosylating the corresponding hydrazide in an essentially anhydrous organic solvent medium using as the source of nitrous acid the alkali metal nitrite complex with the cyclic pentamer of ethylene oxide.

* * * * *

UNITED STATES PATENT OFFICE
CERTIFICATE OF CORRECTION

Patent No. 4,066,684      Dated January 3, 1978

Inventor(s) Linneaus C. Dorman and Edwin C. Steiner

It is certified that error appears in the above-identified patent and that said Letters Patent are hereby corrected as shown below:

Column 2, line 29, delete "of" before the word "mixture" and insert --or--.

Column 3, line 41, delete "axide" and insert --azide--.

Column 5, line 12, delete "N-p-tolysulfonylg-" and insert --N-p-tolylsulfonylg- --.

Signed and Sealed this

Eighteenth Day of April 1978

[SEAL]

Attest:

RUTH C. MASON
Attesting Officer

LUTRELLE F. PARKER
Acting Commissioner of Patents and Trademarks